United States Patent
Silvestri, Jr. et al.

(10) Patent No.: US 11,931,438 B2
(45) Date of Patent: Mar. 19, 2024

(54) SILVER FLUORIDE FORMULATIONS, METHODS AND DEVICES FOR CARIES MANAGEMENT

(71) Applicant: Modern Ideas LLC, Watertown, MA (US)

(72) Inventors: Anthony R. Silvestri, Jr., Plymouth, MA (US); Sunny Skaria, Concord, MA (US); Kenneth Berk, Newton, MA (US)

(73) Assignee: MODERN IDEAS LLC, Watertown, MA (US)

( * ) Notice: Subject to any disclaimer, the term of this patent is extended or adjusted under 35 U.S.C. 154(b) by 0 days.

(21) Appl. No.: 17/591,750

(22) Filed: Feb. 3, 2022

(65) Prior Publication Data

US 2022/0241158 A1    Aug. 4, 2022

Related U.S. Application Data

(60) Provisional application No. 63/145,329, filed on Feb. 3, 2021.

(51) Int. Cl.
| | |
|---|---|
| *A61K 8/21* | (2006.01) |
| *A61C 19/06* | (2006.01) |
| *A61K 8/84* | (2006.01) |
| *A61Q 11/00* | (2006.01) |

(52) U.S. Cl.
CPC ............. *A61K 8/21* (2013.01); *A61C 19/063* (2013.01); *A61K 8/84* (2013.01); *A61Q 11/00* (2013.01); *A61K 2800/87* (2013.01)

(58) Field of Classification Search
CPC ... A61K 8/19; A61K 8/84; A61K 6/69; A61K 8/21; A61K 6/20; A61K 2800/74; A61K 2800/87; A61K 2800/58; A61Q 11/00; A61Q 11/02; A61C 19/063
See application file for complete search history.

(56) References Cited

U.S. PATENT DOCUMENTS

| | | | |
|---|---|---|---|
| 8,658,201 B2 | 2/2014 | Singh et al. | |
| 2008/0011636 A1* | 1/2008 | St. John | A61K 8/19 206/449 |
| 2013/0108982 A1* | 5/2013 | Jodaikin | A61C 19/063 433/80 |

FOREIGN PATENT DOCUMENTS

| | | | |
|---|---|---|---|
| CN | 1929819 | * | 2/2012 |
| WO | 9622078 A1 | | 7/1996 |
| WO | 2005074894 A1 | | 8/2005 |
| WO | WO2013124784 | * | 8/2013 |
| WO | 2017070578 A1 | | 4/2017 |

OTHER PUBLICATIONS

European Patent Office, International Search Report and Written Opinion dated May 16, 2022 for PCT Application No. PCT/US2022/015053 (13 pages).

* cited by examiner

*Primary Examiner* — Lezah Roberts
(74) *Attorney, Agent, or Firm* — BURNS & LEVINSON LLP

(57) ABSTRACT

An oral care formulation includes an aqueous mixture of a water-soluble silver salt, a fluoride reagent, and a water-soluble polymer, the aqueous mixture having a viscosity ranging from about 1000 cPs to about 35,000 cPs. A method of using a fluoride and silver containing formulation, such as silver diamine fluoride, in dental applications includes providing a substrate having the formulation in a solid or semi-solid state on a portion of the substrate, positioning the substrate adjacent to dental areas, and allowing the portion of the substrate with the formulation to contact the dental areas. A disposable applicator for applying the formulation is also disclosed.

12 Claims, 12 Drawing Sheets

SILVER FLUORIDE FORMULATIONS, METHODS AND DEVICES FOR CARIES MANAGEMENT

CROSS-REFERENCE TO RELATED APPLICATIONS

This patent application claims the benefit of U.S. provisional patent application No. 63/145,329, filed Feb. 3, 2021, the disclosure of which is incorporated by reference herein in its entirety.

TECHNICAL FIELD

The present invention relates to fluoride and silver containing formulations, and more specifically for using the formulations in novel ways for caries (i.e., tooth decay) prevention and management in dental applications.

BACKGROUND ART

Tooth decay has been the source of suffering for man since the beginning of time. However, it became a more serious and widespread problem beginning around the 17$^{th}$ through 19$^{th}$ centuries when advanced food production techniques permitted the introduction and widespread inclusion of refined carbohydrates and sugars into the diets of modern man. Dental decay or caries is an infectious bacterial disease of hard tooth structures. The cavity causing bacteria reside in the sticky dental biofilm or plaque that attaches tenaciously to the surfaces of teeth especially in hard to clean areas like the recesses of pits and grooves of back teeth and the smooth surfaces in between teeth. These tooth surfaces represent the location where the vast majority of tooth decay begins and grows. The specific bacteria of the flora of the oral biofilm that cause tooth decay require refined carbohydrates and sugar to thrive which results in a cavity. Wherever these cavity causing bacteria exist in the biofilm on teeth, acid is produced at that location when these bacteria are exposed to sugar and refined carbohydrates, lowering the pH at that specific location. A pH of 4.5 or lower is capable of decalcifying enamel, starting a cavity and destroying teeth.

Silver Diamine Fluoride (SDF) is a medicament that has been used around the world for nearly 100 years in a liquid state to eliminate tooth sensitivity, and to stop and eliminate tooth decay. Silver diamine fluoride kills the bacteria that cause tooth decay and prevents the production of bacterial plaque on the teeth. In the presence of silver diamine fluoride, active cavities will stop growing and new cavities will not form. When silver diamine fluoride is coated on an existing actively growing carious surface, the cavity stops growing. When applied to teeth, silver diamine fluoride is absorbed into the surface of healthy enamel, e.g., to a depth of about 25 µm. The residual silver diamine fluoride in the enamel prevents the bacterial plaque from forming, eliminating cavity causing bacteria and preventing a cavity from developing at that site.

For over 80 years, published articles, products, formulations and clinical applications have extensively used silver diamine fluoride in its liquid state. Silver diamine fluoride is applied to the surfaces of teeth and existing caries for about one minute. It works to stop and prevent cavities without anesthesia, can be applied by paraprofessionals with little to no specialized training and can be applied in non-traditional clinical settings, e.g., schools, nursing homes, etc., without expensive dental equipment. Its effectiveness for caries management is unquestioned.

Silver diamine fluoride has had decades of proven safety with no or low morbidity. In all the years of use, there has not been a reported case of an adverse systemic reaction. In 2014, the Food and Drug Administration (FDA) gave silver diamine fluoride (SDF) approval for use in the United States as a desensitizing agent.

SDF used in dentistry is a highly alkaline, clear liquid with the viscosity of water. Currently used formulations of SDF contain 38% solids (25% silver, 8% ammonia, 5% fluoride) in 62% water. Such a formulation contains 44,800 ppm fluoride ions and has a pH of about 10. Upon exposure to light, the formulation gradually turns black and opaque. Its low viscosity and clarity make it difficult to apply to precise oral cavity locations and, when it turns black, it results in unsightly, often undesirable tooth and soft tissue staining wherever it may have flowed. Its highly alkaline pH and ammonia component make its taste highly disagreeable.

In spite of its considerable cavity fighting benefits, the use of silver diamine fluoride remains low and limited in scope due to its objectionable dark staining of teeth and soft tissue, its highly disagreeable taste, and the difficulty of controlling its application, especially in hard-to-access, high caries prone areas like between the teeth. Also, for currently used liquid formulations, a patient may be exposed to more than the required therapeutic dose due to unwanted drift, run-off, and the inability of the dental clinician to see where the medicament is being placed. Recently a silver diamine fluoride with added blue dye has been marketed to try to overcome one of these objectionable characteristics.

Polyethylenimines (PEIs) are synthetic polymers, commonly available as branched PEIs containing primary, secondary and tertiary amine groups with the ratio of 1:2:1. PEIs are highly basic and positively charged, and have been extensively used as vehicles for non-viral gene delivery and therapy. In the field of microbiology, PEIs not only can enhance the bactericidal efficiency of both hydrophilic and hydrophobic antibiotics, but also serve as a common microbicidal ingredients. They have permeabilizing effects and can disrupt bacterial cell membranes. PEIs incorporated into composite resins or provisional cements have demonstrated a stable and long-lasting antibacterial effect.

The objectionable characteristics of SDF have seriously inhibited its use by dental professionals. A need exists for a material that overcomes the above discussed disadvantages of silver diamine fluoride, using reactants with recognized biocompatibility.

SUMMARY OF EMBODIMENTS

According to embodiments of the invention, an oral care formulation includes an aqueous mixture of a water-soluble silver salt, a fluoride reagent, and a water-soluble polymer, the aqueous mixture having a viscosity ranging from about 1000 cPs to about 35,000 cPs.

In related embodiments, the formulation may further include ammonia. The formulation may have a pH of about 5 to about 8. The fluoride reagent may be selected from the group consisting of hydrogen fluoride, one or more fluoride salts, and combinations thereof. The fluoride reagent may include a fluoride salt selected from the group consisting of silver fluoride, potassium fluoride, sodium fluoride, and combinations thereof. The water-soluble silver salt may be selected from the group consisting of silver nitrate, silver fluoride, and silver acetate. The water-soluble polymer may be a cationic polymer. The water-soluble polymer may include amine groups. The amine groups may include primary amines. The water-soluble polymer may be selected from the group consisting of polyethyleneimine, polyallylamine, polyvinylamine, and combinations thereof. The water-soluble polymer may be polyethyleneimine (PEI). The PEI may include branched PEI. The branched PEI may have a molecular weight from about 1,800 to about 60,000. The branched polyethyleneimine may be present in the oral care formulation at about 15% to about 30% on a per weight basis.

In related embodiments, the water-soluble polymer may be a non-ionic polymer. The non-ionic polymer may be selected from the group consisting of polyvinylpyrrolidine, polyvinyl alcohol, polyethylene oxide, polypropylene oxide, and combinations thereof. The water-soluble polymer may be a polycarboxylic acid. The polycarboxylic acid may be polyacrylic acid. Silver may be present in the oral care formulation at about 15% to about 30% on a per weight basis. Fluoride may be present in the oral care formulation at about 2.0% to about 8.0% on a per weight basis. The water-soluble silver salt may be silver nitrate, the fluoride reagent may be hydrogen fluoride, and the water-soluble polymer may be polyethyleneimine. On a per weight basis, silver may be present at about 15% to about 30%, fluoride may be present at about 2.0% to about 8.0%, and polyethyleneimine may be present at about 15% to about 30%.

In another embodiment of the invention, a method of using a fluoride and silver containing formulation in dental applications includes providing a substrate having the formulation in a solid or semi-solid state on a portion of the substrate, positioning the substrate adjacent to dental areas, and allowing the portion of the substrate with the formulation to contact the dental areas.

In related embodiments, the fluoride and silver containing formulation may include silver diamine fluoride, silver (polyethyleneimine) fluoride, silver (polyallylamine) fluoride, silver fluoride, silver oxide and hydrogen fluoride (HF), silver nitrate and HF and/or silver acetate and HF. The fluoride and silver containing formulation may be an oral care formulation as described above, that includes an aqueous mixture of a water-soluble silver salt, a fluoride reagent, and a water-soluble polymer, the aqueous mixture having a viscosity ranging from about 1000 cPs to about 35,000 cPs.

The method may further include providing a protective cover that covers a portion of the substrate. The protective cover may include a bead, or tube substantially surrounding the substrate and movable with respect to the substrate. Allowing the portion of the substrate to contact dental areas may include moving the protective cover so that the substrate with the formulation is able to contact the dental areas. Allowing the portion of the substrate to contact dental areas may include moving the substrate so that the formulation is able to contact the dental areas. The method may further include applying the formulation in a liquid state to the substrate and heating the liquid to form the solid or semi-solid state. The method may further include applying the formulation in a liquid state to the substrate and allowing the liquid to air dry to the solid or semi-solid state. The method may further include applying the formulation in a liquid state to the substrate and blowing a gas onto the liquid to form the solid or semi-solid state. The method may further include applying the formulation as a powder, or viscous liquid or gel to the substrate and allowing the powder, or viscous liquid or gel to adhere to the substrate. The substrate may, preferably, include cotton, wool, linen, rayon, and/or nylon. Positioning the substrate may include positioning the substrate in an area between two adjacent teeth. Positioning the substrate may include positioning the substrate on a proximal surface, on a chewing surface, adjacent to a chewing surface or at a gum-line surface of a tooth.

In another embodiment of the invention, a disposable applicator for use in dental applications includes a fluoride and silver containing formulation in a solid or semi-solid state, a substrate configured to hold the formulation, and a protective cover configured to cover a portion of the substrate, wherein the applicator is configured to be in a first position that allows a portion of the substrate that holds the formulation to be protected by the protective cover and configured to be in a second position that allows a portion of the substrate that holds the formulation to be exposed such that the formulation is dispensed when adjacent to dental areas.

In related embodiments, the fluoride and silver containing formulation may include silver diamine fluoride, silver (polyethyleneimine) fluoride, silver (polyallylamine) fluoride, silver fluoride, silver oxide and hydrogen fluoride (HF), silver nitrate and HF and/or silver acetate and HF. The fluoride and silver containing formulation may further include a polymeric stabilizer, such as polyethyleneimine, polyallylamine, and/or silver fluoride conjugates with polyvinyl pyrrolidinone, polyacrylic acid, polyvinyl alcohol, polyethylene oxide, and/or polypropylene oxide. The protective cover may substantially surround the substrate. The protective cover may include a bead or tube substantially surrounding the substrate and may be movable with respect to the substrate so that the applicator is able to change from the first position to the second position. The substrate may be able to stretch so that the applicator is able to change from the first position to the second position. The substrate may include cotton, wool, linen, rayon, and/or nylon. The disposable applicator may further include a positioning tool configured to hold the substrate and allow the substrate to be positioned on or adjacent to the dental areas. For example, the positioning tool may include a knot in the substrate configured to limit relative motion of the protective cover with respect to the substrate.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Figure 1:
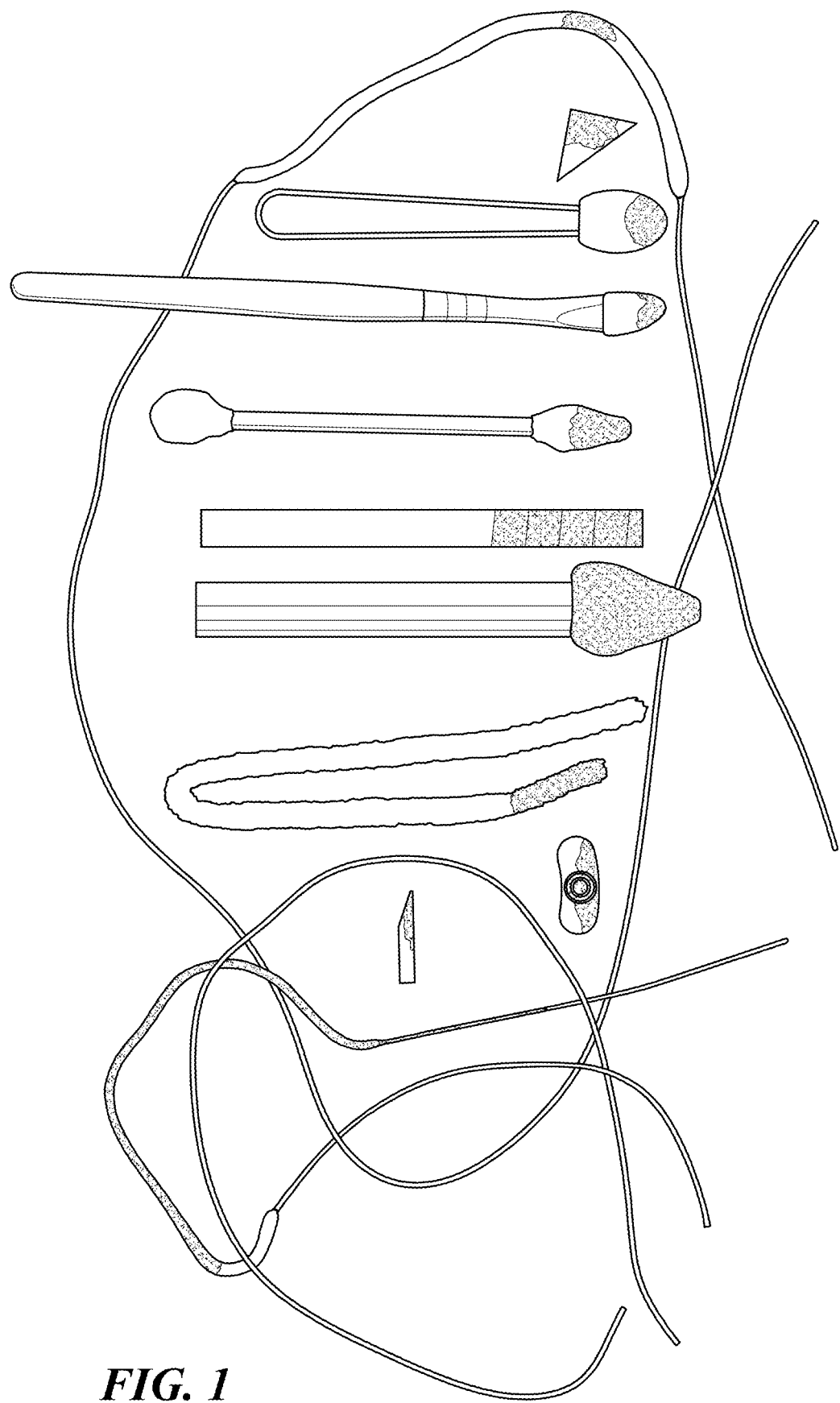
FIG. 1 shows various substrates having solid silver diamine fluoride on a portion of the substrate according to embodiments of the present invention.

Definitions. As used in this description and the accompanying claims, the following terms shall have the meanings indicated, unless the context otherwise requires.

A "viscous" liquid is a liquid having a measured viscosity of greater than about 1000 cPs.

A "semi-solid" is a viscous liquid or gel.

A "fluoride reagent" is a reagent providing fluoride ions, for example a fluoride salt or hydrogen fluoride.

A "silver and fluoride containing formulation," is a formulation containing silver and fluoride ions. Such formulations include silver diamine fluoride (SDF) and silver polyethyleneimine fluoride (SPF).

A "proximal" surface of a tooth is a surface of the tooth that is facing an adjacent tooth.

Embodiments of the present invention provide a silver and fluoride containing formulation (SFF) capable of localized application by virtue of having a solid or semi-solid, e.g., viscous or gel-like consistency, and a device and method of using such formulations in dental applications.

Some embodiments make use of fluoride and silver containing formulations in a solid or semi-solid form. For such embodiments, the formulation in a solid state or semi-solid state is first applied on or absorbed into a substrate. The silver and fluoride containing formulation may be applied to the substrate in a liquid state and then dried or partially dried on the substrate or may be applied to the substrate in its solid or semi-solid form, e.g., as a powder or viscous liquid or gel, and adhered to the substrate. Application in a solid or semi-solid form allows the material to hold or adhere sufficiently to the substrate, which allows placement in a desired area and its use in a wider range of clinical applications and its application in a neater, more precise and controlled way than would be possible for application of a liquid formulation. The precise, controlled application of the solid or semi-solid silver and fluoride containing formulation greatly limits drift and run-off, reducing the unintended excess dose a patient typically receives during current application treatment techniques using liquid silver fluoride diamine. Thus, embodiments of the present device and method permit quick, easy and neat use of this highly effective anti-cavity silver and fluoride containing formulations to all tooth surfaces, and permit the selective targeting of these tooth surfaces in a preventive manner.

In embodiments of the present invention, the solid or semi-solid silver and fluoride containing material on the substrate does not need to be pre-moistened with water or pre-activated for its effective use on teeth. There is typically sufficient ambient moisture in the tooth and mouth to activate the material in-situ once it is positioned in the appropriate location on the tooth surface, e.g. in between teeth, at the root, on the chewing surfaces and gum-line surfaces of teeth. If sufficient moisture is not present in the mouth to facilitate medicament transfer on dental structures due to unusual intra-oral dryness, the patient may rinse and spit out water prior to application. This leaves sufficient residual water on dental surfaces for activation during application.

For some embodiments, the silver and fluoride containing formulations include a silver coordination complex, e.g., having coordinating ligands such as ammines, amines, carbenes, and/or phosphenes.

In a preferred embodiment, polyethyleneimines (PEIs), particularly branched PEIs provide the necessary coordinating ligands. Branched PEIs are synthetic polymers containing primary, secondary and tertiary amine groups generally in the ratio of around 1:2:1. They are highly basic and positively charged, and have been extensively used as a vehicle for non-viral gene delivery and therapy. In the field of microbiology, PEIs can enhance the bactericidal efficiency of both hydrophilic and hydrophobic antibiotics, and can also serve as a common microbicidal ingredient. PEIs have permeabilizing effects and can disrupt bacterial cell membranes. PEIs incorporated into composite resins or provisional cements have demonstrated a stable and long-lasting antibacterial effect.

When PEI is incorporated in a formulation with fluoride and silver nitrate according to embodiments of the present invention, the formulation can be tuned to control both the viscosity and the color of the solution by controlling the PEI concentration. At lower concentrations of PEI, the formulation provides a clear solution with grey/black specks throughout and a viscosity of less than 50 cPs (centipoise), while at higher concentrations an opaque black material results with a viscosity in the range of 1,000 cPs to 35,000 cPs. This higher viscosity formulation proved excellent for application with a dental applicator to the biting surfaces of posterior teeth as well as to gum-line areas of teeth. Additionally, the higher viscosity formulation can be effectively deposited on the proximal surfaces of teeth by means of a disposable application having an elastic or multi-strand thread, e.g., by dipping the center area, or by touching the formulation to a plastic flosser. Such a formulation of PEI, fluoride, and silver nitrate is designated as silver polyethyleneimine fluoride, or SPF, in the discussion below.

The SPF formulation may include, on a per weight basis, about 15% to about 30% silver ion, about 15% to about 30% branched PEI, and about 2% to about 8% fluoride. The ion is provided by the silver nitrate solution and the fluoride is provided by hydrogen fluoride. Such embodiments provide viscous solutions with a gel-like consistency that promote adhesion to tooth surfaces, and allow superior localization during application.

Embodiments of the present invention also provide a disposable applicator that may be formed using various substrate materials and shapes, such as shown in FIG. 1. The disposable applicator dispenses the fluoride and silver containing formulation in a controlled, reproducible manner while also reducing the unwanted side effects. The disposable applicator comes preloaded with a fluoride and silver containing formulation in a solid or semi-solid state, e.g., dried or partially dried solid state or in a gel semi-solid state, on a substrate. The disposable applicator permits controlled, targeted application of the fluoride and silver containing formulation to high caries susceptible areas of the dentition previously inaccessible to dentists, like the proximal surfaces of teeth. The fluoride and silver containing material is minimally visible or not visible at all between teeth if that area is targeted precisely. Cavity causing bacteria reside in the bacterial biofilm that sticks to the smooth enamel surfaces in between teeth. If no biofilm forms there, no caries can form. Applying a fluoride and silver containing formulation to the proximal surfaces of teeth would stop decay from growing and prevent new cavities from forming there.

Embodiments of the present invention disclose using solid or semi-solid fluoride and silver containing formulations in a novel way and disclose using fluoride and silver containing formulations preloaded in a novel device that specifically targets and prevents the formation of the biofilm that normally grows on tooth surfaces between teeth. The method is quick, painless, and convenient. Embodiments eliminate or minimize discoloration in visible areas and eliminate the highly disagreeable taste associated with uncontrolled liquid application of silver diamine fluoride.

Embodiments of the present invention may be used for interproximal (between the teeth) applications and for open surface applications, for example, the chewing surfaces, surfaces adjacent to chewing surfaces, and gum-line surfaces of teeth, including root surfaces. In the interproximal application or treatment, the solid or semi-solid fluoride and silver containing formulation may be dried onto or adhered to a substrate, such as a thin strip of "cloth" or "ribbon", preferably a substrate that is flexible or elastic enough to adapt readily, without tearing, to the contours of the interproximal space. In the open surface application or treatment, the fluoride and silver containing formulation may be dried onto or adhered to a substrate, such as a cotton ball or foam pellet, which may be affixed to a more rigid applicator for its precise placement on the open surface of teeth.

FIG. 1 shows various substrates having solid or semi-solid fluoride and silver containing formulations (black areas) on a portion of the substrate according to embodiments of the present invention. The substrates may include any substrate sufficiently able to hold the solid or semi-solid fluoride and silver containing formulation material in place or allow the fluoride and silver containing formulation material to sufficiently adhere to the substrate so that the fluoride and silver containing formulation may be accurately applied to the desired dental areas, such as an absorbent material or coatable substrate. For example, suitable substrates may include cotton, wool, linen, rayon, and/or nylon, although other materials may be used, such as any fabric material.

The fluoride and silver containing formulation may be applied to the substrate in any number of ways. For example, the formulation may be applied in a liquid state and then dried or partially dried to form the solid or semi-solid on the substrate according to embodiments of the present invention. The liquid may be dried or partially dried by blowing air or another gas onto the liquid, heating the liquid, with or without blowing the air or gas, or just allowing the liquid to air dry. Alternatively, the fluoride and silver containing formulation may be applied to the substrate in its solid or semi-solid form, e.g., as a powder or gel, and trapped in or adhered onto the substrate. For example, the fluoride and silver containing formulation may be permitted to dry to a solid or semi-solid state prior to application on the substrate and subsequently applied to the substrate in its solid or semi-solid form. In some embodiments, fluoride and silver containing formulations in the form of a viscous liquid may be applied directly to the substrate, and may be stored in that form, or may be applied immediately to dental areas. The fluoride and silver containing formulation in the form of a viscous liquid may include polyethyleneimine, which includes SPFs. The liquid, solid or semi-solid fluoride and silver containing formulation may be dispensed onto a substrate in any number of other ways.

Figure 2:
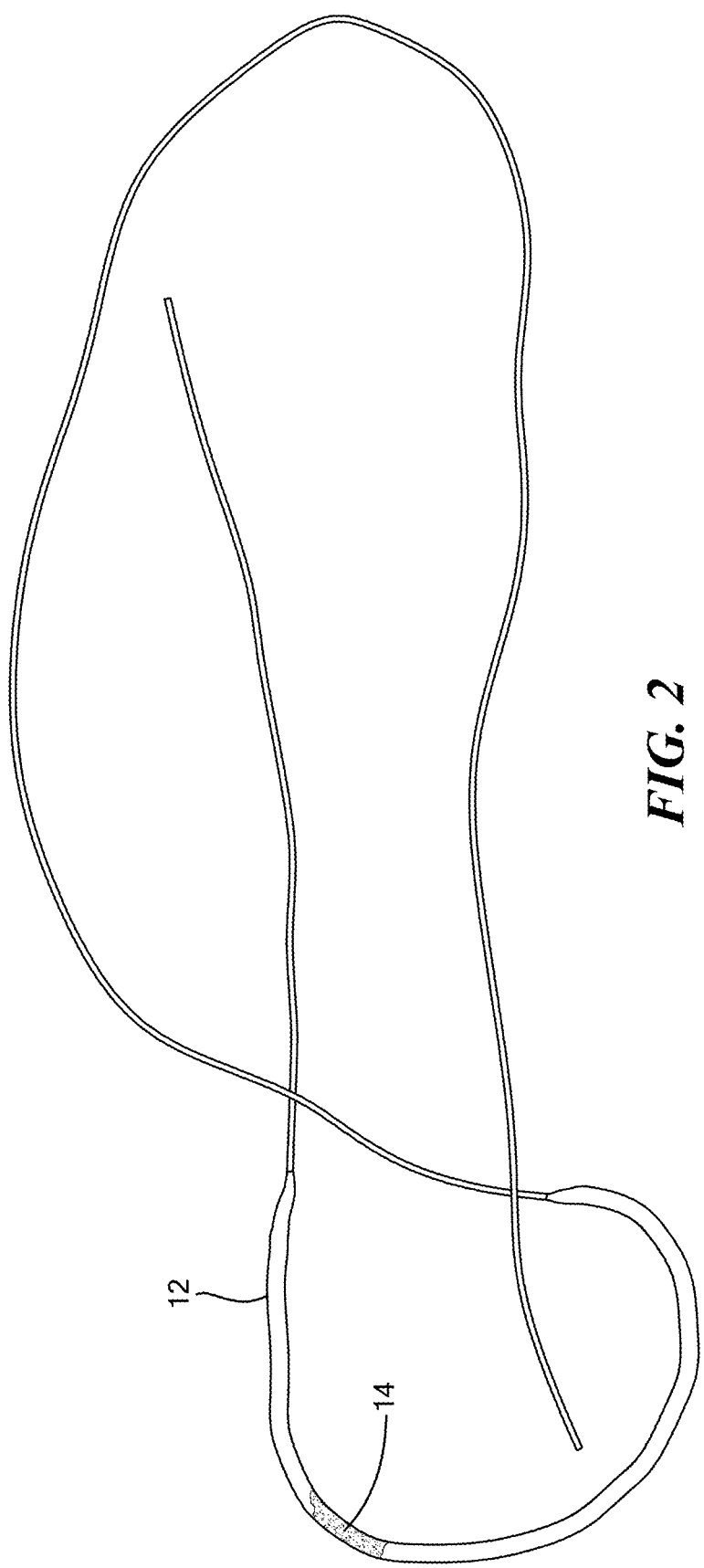
FIG. 2 shows a substrate with solid silver diamine fluoride that may be used in an interproximal application according to embodiments of the present invention.

FIG. 2 shows a substrate 12 with a solid or semi-solid fluoride and silver containing formulation 14 present on a portion of the substrate that may be used in an interproximal application between the teeth according to embodiments of the present invention.

Figure 3:
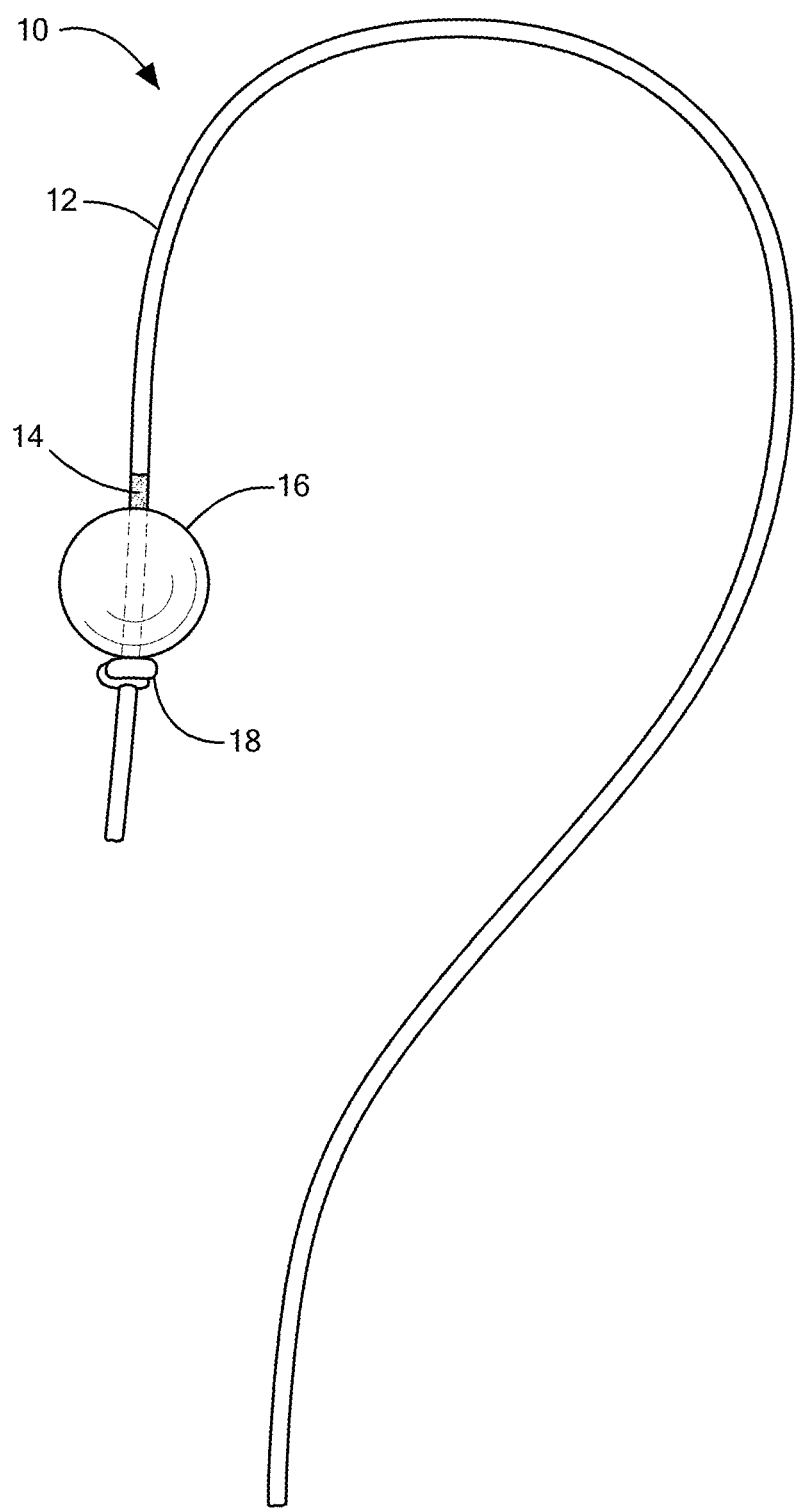
FIGS. 3 and 4 show a disposable applicator with a protective cover according to embodiments of the present invention.
Figure 4:
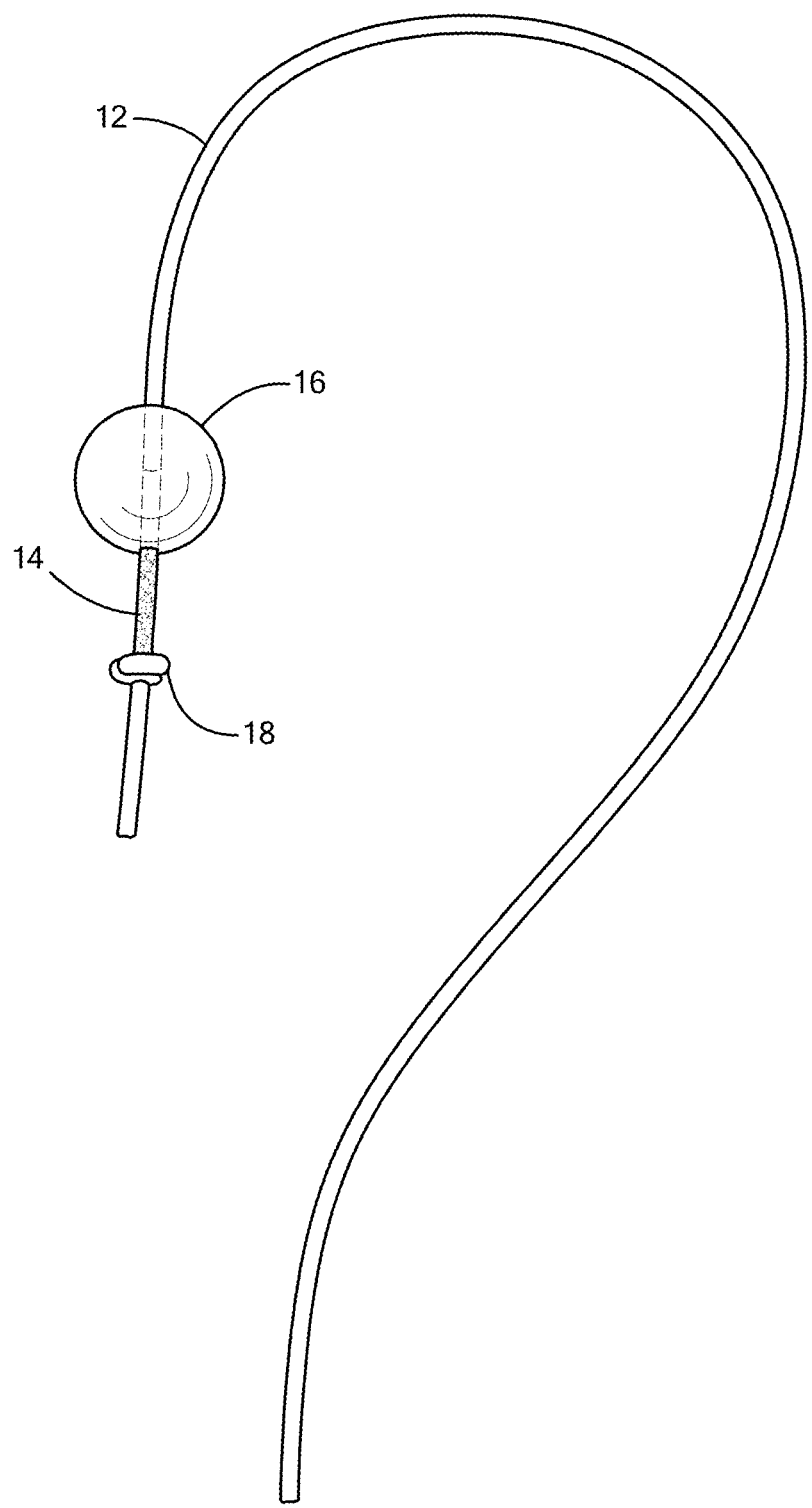
Figure 5:
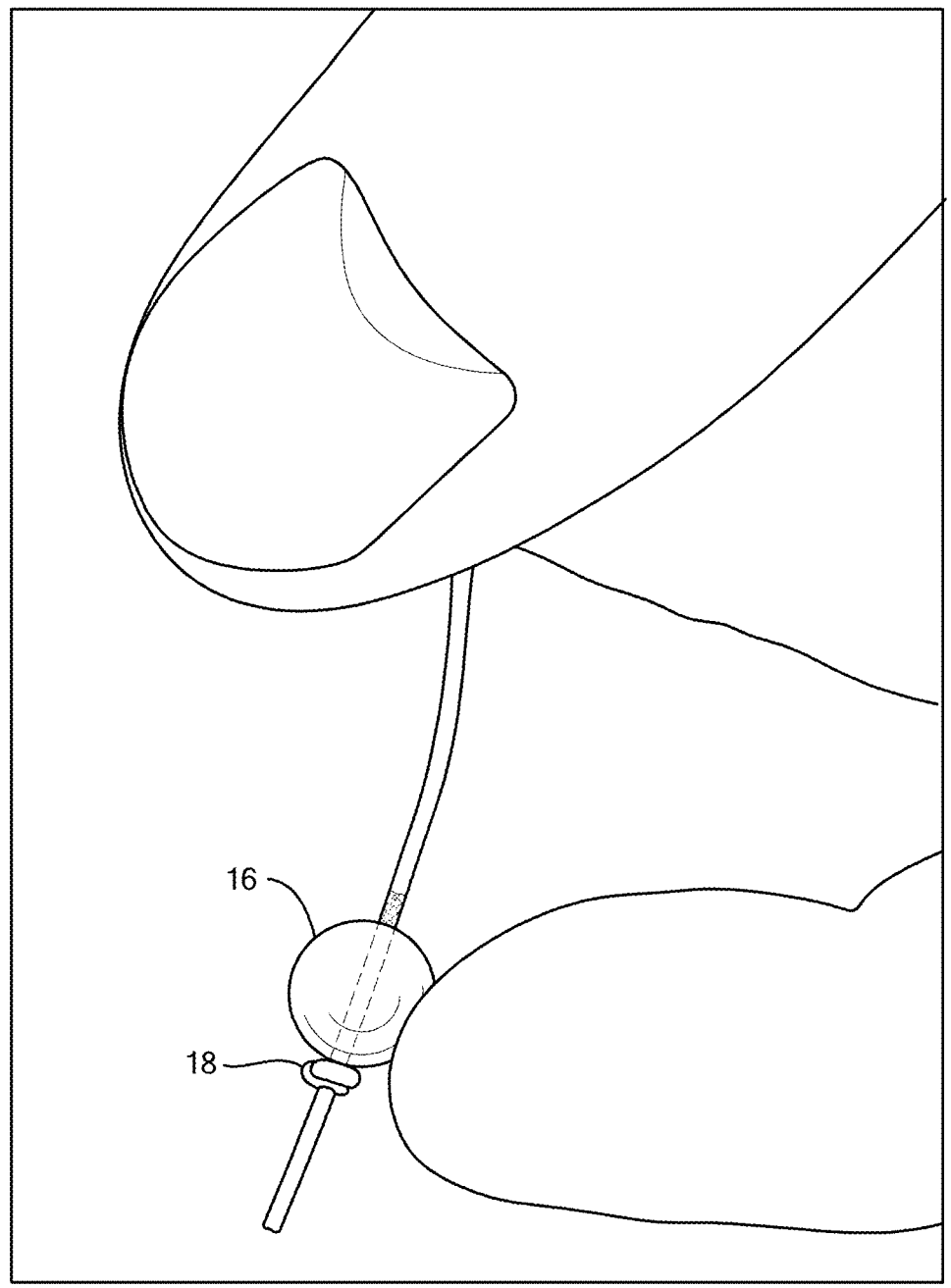
FIGS. 5 and 6 show a disposable applicator with a protective cover according to embodiments of the present invention.
Figure 6:
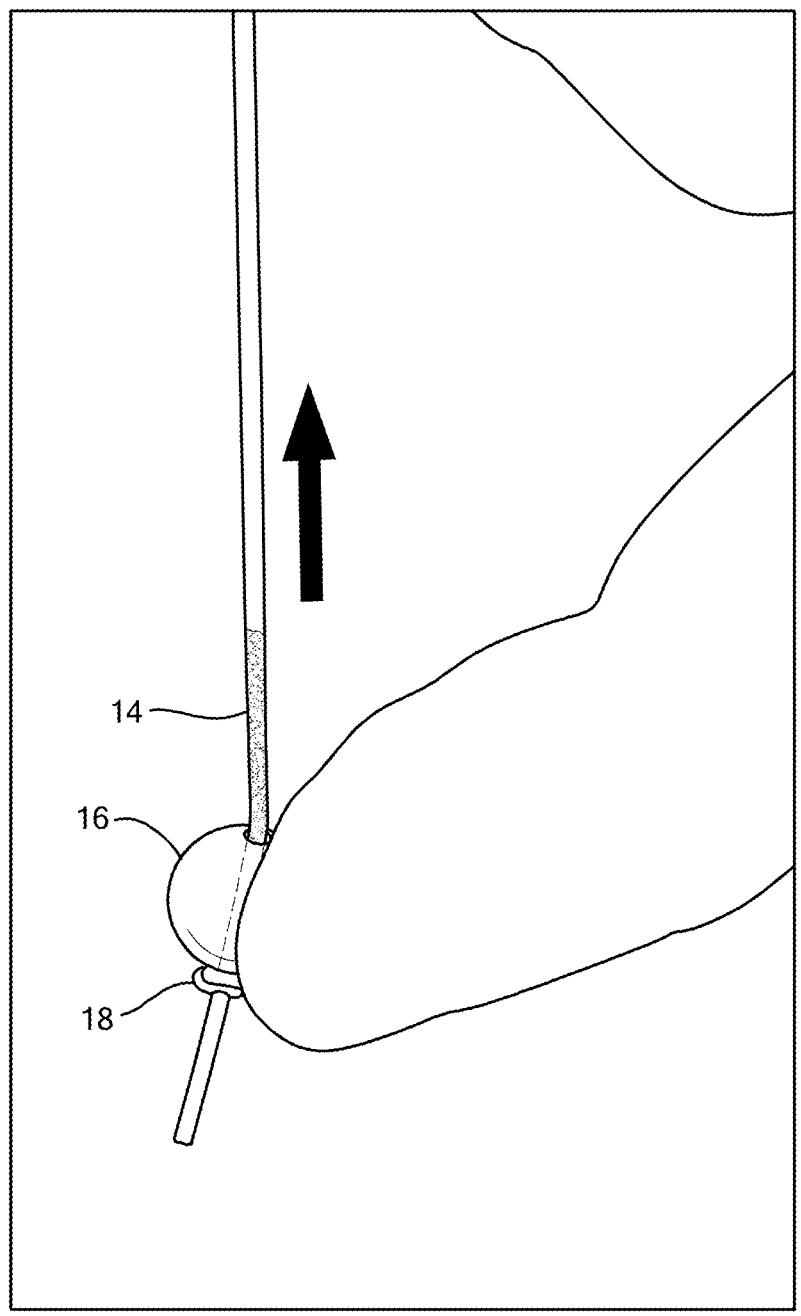

FIGS. 3 through 8 show a disposable applicator 10 according to embodiments of the present invention. The disposable applicator 10 includes a substrate 12 having a fluoride and silver containing formulation 14 in a solid or semi-solid state on a portion of the substrate 12. The applicator 10 further includes a protective cover 16 configured to cover a portion of the substrate 12. For example, the protective cover 16 may be a bead, tube or other structure that substantially surrounds, and is movable with respect to, the substrate 12. For example, the protective cover 16 may slide along the substrate 12 or the substrate 12 may be stretched or expanded. In FIG. 3, the protective cover 16 is shown covering or substantially covering one portion of the substrate 12 that includes the fluoride and silver containing formulation 14. In FIG. 4, the protective cover 16 is shown moved to a different position on the substrate 12 so that at least one portion of the substrate 12 that includes the fluoride and silver containing formulation 14 is exposed. This configuration allows a portion of the substrate 12 to be protected from contacting its surroundings with the protective cover 16 in one position and exposes at least one portion of the substrate 12 in a second, different position. The disposable applicator 10 may optionally include one or more knots 18, stoppers or other means for ensuring that the relative motion of the protective cover 16 with respect to the substrate 12 is limited along the substrate 12, in one or both directions. FIGS. 5 and 6 show how the protective cover 16 may also be used to hold one end of the substrate 12 in place while the other end is pulled so that the substrate 12 is moved or stretched with respect to the protective cover 16, exposing a portion of the substrate 12 that includes the fluoride and silver containing formulation 14. For example, FIG. 5 shows the protective cover 16 held in place by hand in one position and FIG. 6 shows the other end of the substrate 12 pulled by hand so that the substrate 12 is stretched or lengthened and at least a portion of the substrate 12, that includes the fluoride and silver containing formulation 14, is exposed in a second position, so that the protective cover 16 is no longer protected.

Figure 7:
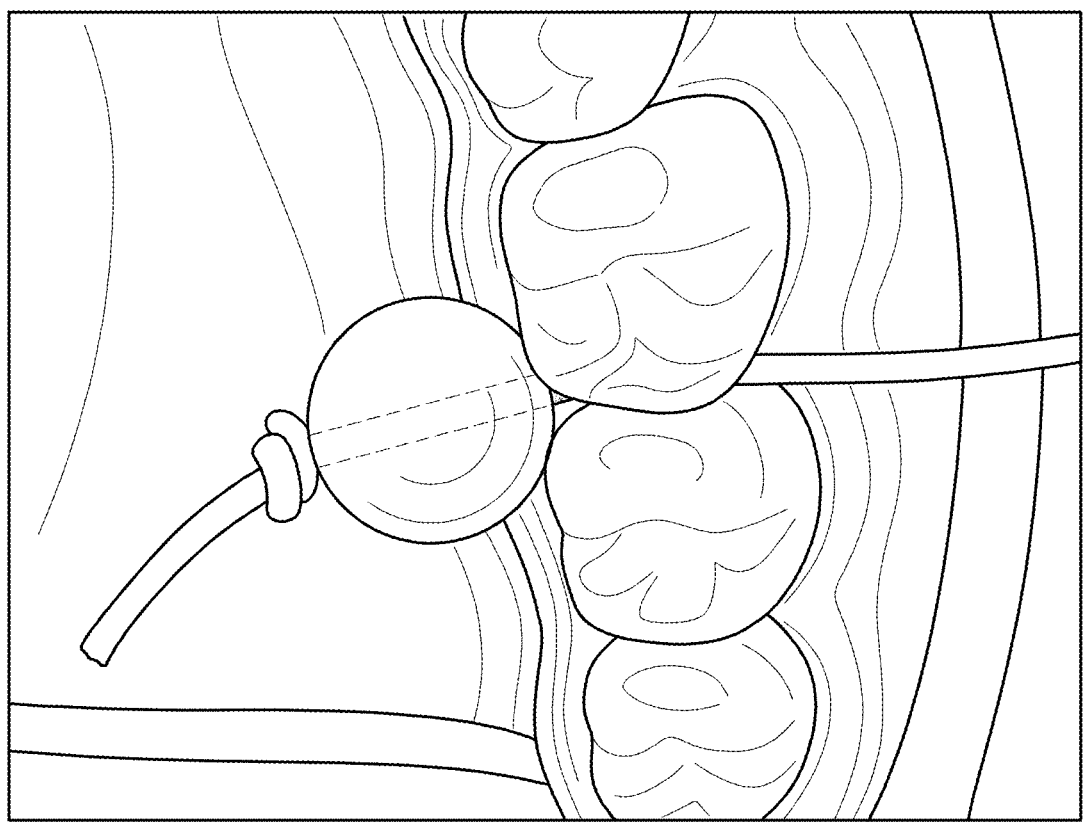
FIGS. 7 and 8 show a disposable applicator with a protective cover between plastic teeth according to embodiments of the present invention.
Figure 8:
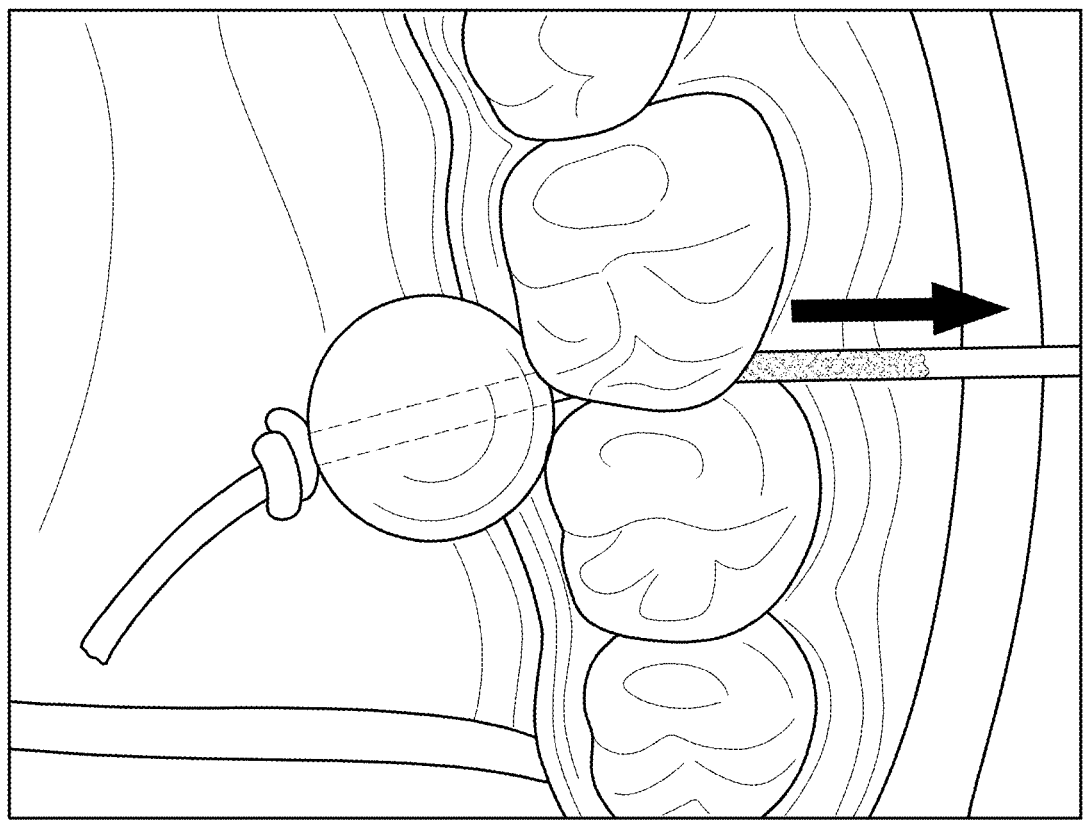

FIGS. 7 and 8 show a disposable applicator 10 positioned between two adjacent teeth according to embodiments of the present invention. FIG. 7 shows the disposable applicator 10 with the protective cover 16 positioned against the teeth and used as a stopper so that the disposable applicator 10 is positioned in the appropriate dental location with the fluoride and silver containing formulation 14 protected under the protective cover 16. FIG. 8 shows the disposable applicator 10 when the substrate 12 has been pulled or stretched so that at least a portion of the fluoride and silver containing formulation 14 is exposed and contacts the dental area between the teeth so that the fluoride and silver containing formulation is dispensed to the dental area.

Figure 9:
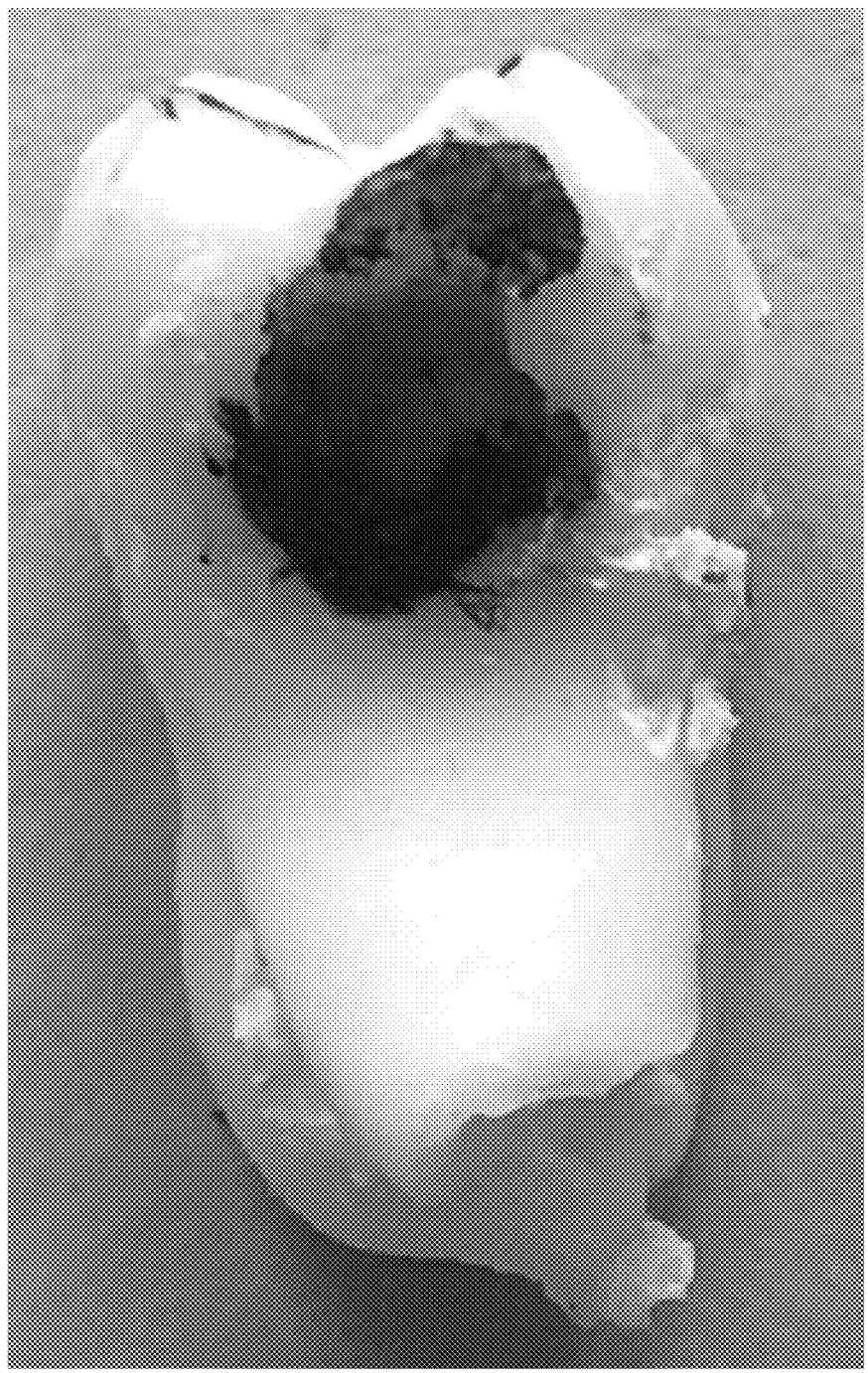
FIG. 9 shows silver diamine fluoride staining on a proximal surface of an extracted tooth after a disposable applicator with silver diamine fluoride was used according to embodiments of the present invention.

FIG. 9 shows the limited, controlled silver diamine fluoride (SDF) staining that occurs on a proximal surface of an extracted tooth avoiding staining on more visible areas after a disposable thread- or floss-like applicator 10 is positioned against the tooth according to embodiments of the present invention. In this case, the silver diamine fluoride was air dried on the substrate 12 for 48 hours in an ambient environment. The disposable applicator 10 transferred the silver diamine fluoride onto the extracted human tooth by rubbing the substrate 12 with the silver diamine fluoride against the tooth for about one minute. As shown in FIG. 9, the silver diamine fluoride only stained the proximal surface of the tooth, in a confined target area, showing the transferability of the silver diamine fluoride to enamel and cementum. The precisely targeted, stained proximal area of the tooth (e.g., between teeth) may be hidden from view and applied exactly where treatment is needed to prevent caries from developing.

EXAMPLES

As mentioned above, fluoride and silver containing formulations, including silver diamine fluoride (SDF) and silver (polyethyleneimine) fluoride (SPF), may be used in embodiments of the present invention. In addition to SDF and SPF, silver and fluoride containing formulations may include other combinations of water-soluble silver salts and fluoride reagents. For example, fluoride and silver containing formulations may include water-soluble polymers. Suitable fluoride and silver containing formulations may include silver diamine fluoride (SDF), silver (polyethyleneimine) fluoride, silver (polyallylamine) fluoride, silver fluoride, and/or a combination of silver and fluoride reagents such as silver oxide and hydrogen fluoride (HF), silver nitrate and HF, silver acetate and HF or a combination of one or more of these salts.

When present in fluoride and silver containing formulations, water-soluble polymers may act as viscosity modifiers, and may also form and/or stabilize complexes with silver ions, and aid in obtaining solid or semi-solid coatings on applicators. Suitable water-soluble polymers may be chosen from cationic silver complexing polymers, such as polyethyleneimine, polyallylamine, and/or silver fluoride conjugates, together with one or more nonionic or anionic water soluble polymers, such as polyvinyl pyrrolidinone, polyacrylic acid, polyvinyl alcohol, polyethylene oxide, and/or polypropylene oxide.

As a clear liquid, silver diamine fluoride does not immediately stain healthy tooth structures dark brown. A prolonged period of time is needed before stains become apparent. Carious tooth structure does minimally stain during application and continues to darken with time as the silver oxidizes in the mouth. When applied on teeth in the mouth, the clinician will not notice that healthy tooth structure and soft tissue have been stained and cannot appreciate how much discoloration will occur after the passage of time due to the oxidation process of the silver. Many references and clinicians have under-reported the degree with which silver diamine fluoride stains healthy tooth structures.

Figure 10:
FIG. 10 shows the staining of surfaces of an extracted tooth after liquid silver diamine fluoride was used on the tooth using a foam applicator.

To test that tooth structures do stain when silver diamine fluoride is applied to teeth, human extracted natural teeth were coated with the silver diamine fluoride. Several teeth, some with active caries, some with initial caries and surface hypocalcifications, and others with no caries at all, were painted with liquid silver diamine fluoride. These teeth were subsequently exposed to strong visible light to speed up the oxidation process and within minutes a dark brown stain became apparent over all tested surfaces (see FIG. 10).

Figure 11:
FIG. 11 shows the deep penetrating stain of an extracted, sectioned tooth after liquid silver diamine fluoride was used on the tooth.

The results from these early tests clearly showed silver diamine fluoride has the potential to stain all tooth structures including healthy enamel. In order to determine whether the stain was only a surface phenomenon or something deeper, the teeth were sectioned and examined under magnification. FIG. 11 shows one example of a sectioned tooth.

The penetration of the brown staining is clear evidence of silver penetration. Silver is the anti-cavity, antibacterial, active ingredient of silver diamine fluoride and its presence will inhibit the formation of cavity causing bacterial plaque, stop a cavity where it exists and prevent a cavity where it does not exist. This is extremely significant since if a brown stain occurs on a tooth from silver diamine fluoride, it is clear evidence that silver is present and that area will be protected from caries development. As shown in FIG. 11, brown staining on a tooth surface is evidence of deeper penetration and is more than a superficial surface phenomenon.

A dissecting microscope was used to confirm the brown stain penetrated well below the surface, supporting the findings of Suzuki (1974) (Suzuki T, Nishida M, Sobue S et al. Effects of diamine silver fluoride on tooth enamel. J Osaka Univ Dent Sch 1974 14: 61-72) that fluoride and silver ions from diamine fluoride penetrate enamel to a depth of ~25 microns. To test further that the stain was more than a surface phenomenon, the teeth were subjected to aggressive washing with soap and water as well as soaking in bleach for several minutes to evaluate whether the stain either disappeared or faded. No change in color was noted on any tooth surface.

Unfortunately, to date, silver diamine fluoride is not often used to prevent (or even arrest) caries often despite its proven effectiveness against bacterial biofilm development and caries arresting action due to its severe disagreeable staining. The potential for silver diamine fluoride to decrease the suffering from tooth decay is significant if novel ways to use it efficiently, neatly and in a targeted way are devised, such as described in embodiments of the present invention.

Further tests were conducted to find ways to improve the use of silver diamine fluoride according to embodiments of the present invention in order to avoid widespread uncontrolled staining. The goal was to use silver diamine fluoride according to embodiments of the present invention in a more precise, targeted fashion that clinicians and patients could accept more readily in its application and use. Tests were conducted in which the physical properties of liquid silver diamine fluoride were changed from the liquid state to a solid or semi-solid state (e.g., dried solid or gel).

A solid or semi-solid silver diamine fluoride provides a more precise method of application of the medicament to tooth surfaces and gives hope that refinements could provide novel methods for precise targeting of tooth surfaces previously impossible without undesirable widespread staining.

Figure 12:
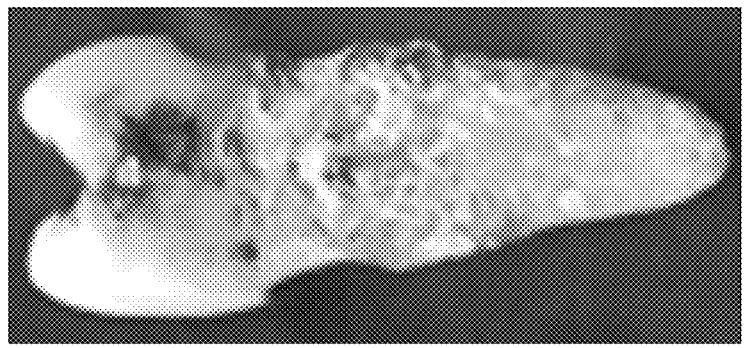
FIG. 12 shows the staining of an extracted tooth after solid silver diamine fluoride was applied on the tooth from a paper applicator according to embodiments of the present invention.
Figure 12:
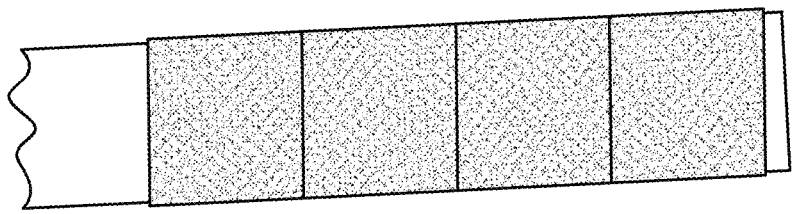
Figure 12:
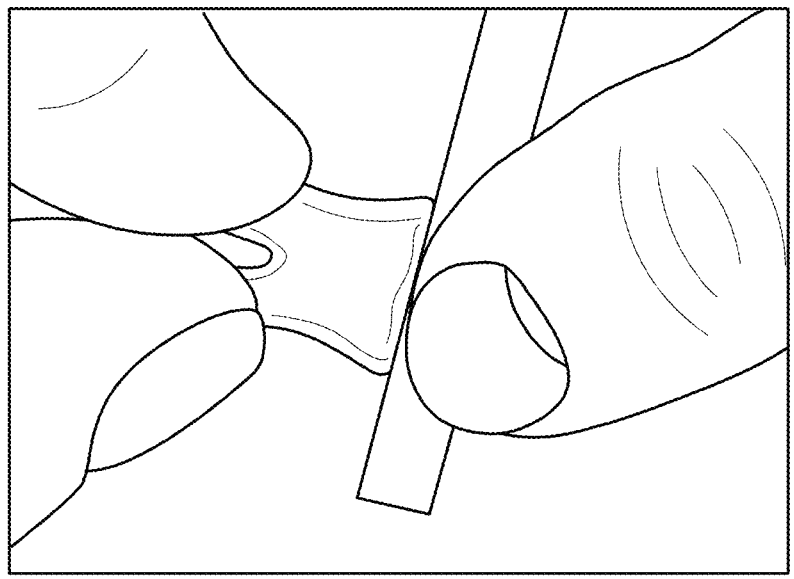
Figure 12:
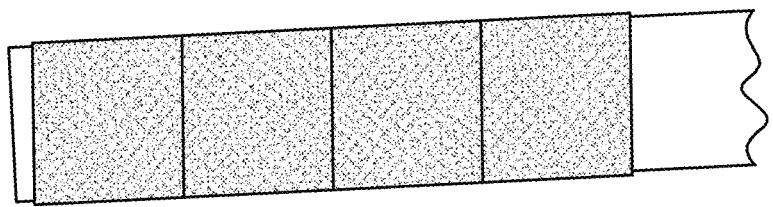

Another encouraging early test evaluated the transferability of solid or semi-solid silver diamine fluoride when a sponge was used as the substrate. More tests were performed to determine if solid or semi-solid silver diamine fluoride was transferable to healthy enamel and other tooth surfaces using human extracted teeth. FIG. 12 shows the results of initial test applying a solid or semi-solid silver diamine fluoride from a strip of material to dry tooth structures. A paper applicator with a flock covering was allowed to absorb one drop of liquid silver diamine fluoride and subsequently allowed to dry for 24-48 hours. The applicator was then pressed against a human extracted tooth for about one minute with slight pressure. Transferability was simple, fast and quite controlled without widespread spillage. Further embodiments using different applicators were tested and the transferability to tooth structures was found to be quick, easy and targeted.

Since the second most common location of caries is between the teeth, a place extremely difficult to accurately target without spillage with liquid silver diamine fluoride (and typically not visible to the eye), novel devices were sought to apply solid or semi-solid silver diamine fluoride. Tests were conducted on human extracted teeth mounted in plaster to assess the ability of devices to target this difficult to access area between teeth. Brown stains confirmed the presence of silver on the proximal areas confirming that this area between the teeth was successfully targeted using the novel device without unsightly staining of silver diamine fluoride on surrounding more visible buccal and lingual areas of the teeth due to spillage.

Materials and Methods:

Silver nitrate, silver fluoride, branched polyethyleneimines of MW 1800 & MW 60000) were obtained from Sigma Aldrich (Milwaukee, Wis., US); 50 wt % hydrofluoric acid was obtained from Puritan Products (Bethlehem, Pa., US). Sodium fluoride and potassium fluoride were obtained from Alfa Aesar, Haverhill, Mass., US.

The viscosity of the oral care formulations prepared was determined by Brookfield Cone-Plate viscometer, Spindle #52 (AMETEK HB Viscometer; Brookfield Industries, Middleboro, Mass., US). The viscosity measurements were done at 25° C. at a RPM of 20 and the values are expressed in centipoise (cPs). The fluoride concentration of the oral care formulations was determined using an ISE Fluoride ion specific electrode and the pH of the formulation was determined by OAKTON pH meter (Oakton Instruments, Vernon Hills, Ill., US).

Example 1: Preparation of Silver Diamine Fluoride Solution

A silver diamine fluoride solution was prepared by dissolving 1.87 g of Silver Fluoride in 5 mL of a 10% Ammonia solution followed by the addition of 0.2 g hydrofluoric acid (added slowly). A clear solution with a pH of 10 was obtained. The concentration of silver diamine fluoride was in the range of 35-37 wt. % and contained 23.4% silver; 5.4% fluoride and 7.2% ammonia.

Example 2: Preparation of Silver Polyethyleneimine Fluoride Conjugate

A silver polyethyleneimine fluoride solution was prepared by reacting a 2.54 g silver fluoride (20 mmole) (dissolved in 2.5 mL distilled water) with a solution of 2.5 g of polyethyleneimine (Molecular weight 60,000) in 2.5 mL distilled water. The product contained 21.6% silver; 3.8% fluoride and 25% polyethyleneimine. The product was very soluble in water. The product was highly viscous, stringy and very dark grey. It was very hard to dispense from a bottle and not acceptable for our use.

Examples 3 to 6: Additional Preparations of Silver Polyethyleneimine Fluoride from Silver Fluoride Additional silver polyethyleneimine fluoride examples are summarized in Table I:

TABLE I

Silver polyethylene imine formulations with silver fluoride.

| | Formulation | | |
|---|---|---|---|
| Exp # | Polymer/ amount | AgF (66 wt. % in water) | Results/Comments |
| 3 | 1.0 g PEI( MW1800) | 0.50 g (0.28 g Ag and 0.05 g F) | This is a formulation with 18.7% silver ions and 3.33% Fluoride ions; The reaction is exothermic; the product is brown colored and is too thin with viscosity less than 50 cP. |
| 4 | 1.0 g (PEI MW1800) | 1.0 g (0.56 g Ag 5.6 m 0.10 g F) | This is a formulation with 28.5% silver ions and 5.0% Fluoride ions; the product is dark brown colored and too stringy; it is hard to dispense from a bottle and difficult to apply on tooth. The product is soluble in water |
| 5 | 1.0 g (PEI, MW 60000, 50 v/v solution in water) | 0.5 g (0.28 g Ag and 0.05 g F) | This is a formulation with 18.7% silver ions and 3.33% Fluoride ions; The product is dark brown colored and very stringy, difficult to dispense from a bottle |
| 6 | 1.0 g (PEI , MW 60000, 50 wt. % solution in water) | 1.0 g 0(.56 g Ag 5.6 m | This is a formulation with 28.5% silver ions and 5.0% Fluoride ions; The product is very black and very stringy, it is difficult to dispense from a bottle |

Example 7: First Formulation of Silver Polyethyleneimine Fluoride from Silver Nitrate A solution of 66.6 wt. % silver nitrate (Solution A) was prepared by dissolving 10.0 g silver nitrate (59 mmol) in 5 mL distilled water. Solution B was prepared by adding 10.0 g polyethyleneimine (molecular weight 60,000; 50% solution in water), and hydrogen fluoride (2.4 g; 50% HF; 59 mmol) at under ice cold temperature (0° C.-5° C.) and made up to 15 mL. The oral care formulation was prepared by mixing Solution A (15 mL) with solution B (15 mL) at room temperature (22° C.) in a 100 mL plastic beaker. The reaction was exothermic and a milky white emulsion formed which eventually turned to dark grey. The product was viscous and the material grey-black. The material held very well on the applicators and could be very precisely applied at the targeted area(s) of the tooth using a thin applicator, an elastic or multi-strand thread, or a plastic flosser. The viscosity of the material was 368 cPs measured with a cone plate viscometer at a RPM of 20 and 25° C. (AMETEK HB Viscometer, Brookfield, Middleboro, Mass., US). The pH of the viscous solution was 5.02 measured on a Okton pH meter. This oral care formulation contained 21.5% silver; 16.7% polyethyleneimine and 4% Fluoride ions. The fluoride ions, were measured using an ISE Fluoride specific electrode. The product was completely soluble in water.

Example 8: Second Formulation of Silver Polyethyleneimine Fluoride from Silver Nitrate A solution of 66.6 wt. % silver nitrate (Solution A) was prepared by dissolving 10.0 g silver nitrate (59 mmol) in 5 mL distilled water. Solution B was prepared by adding 12.5 g polyethyleneimine (molecular weight 60,000; 50 wt. % solution in water), and hydrogen fluoride (2.4 g; 50% HF; 59 mmol) at under ice cold temperature (0° C.-5° C.) and made up to 18 mL. The oral care formulation was prepared by mixing Solution A (15 mL) with solution B (18 mL) at room temperature (22° C.) in a 100 mL plastic beaker. The product was viscous and the material was brown-black in color. The material held very well on the applicators and could be very precisely applied at the targeted area of the tooth using a thin applicator, an elastic or multi-strand thread, or a plastic flosser. The viscosity of the material is 35,380 cPs measured at 20 RPM at 25° C. The pH of the viscous solution was 6.02. The oral care formulation contained 19.5% silver; 19.0% polyethyleneimine and 3.6% fluoride ions. The product was completely soluble in water. The material held very well on the applicators and could be very precisely applied at the targeted area of the tooth using a thin applicator, an elastic or multi-strand thread, or a plastic flosser. The product could be easily dried on an applicator.

Example 9: Third Preparation of Silver Polyethyleneimine Fluoride from Silver Nitrate A solution of 66.6 wt. % silver nitrate (Solution A) was prepared by dissolving 17.0 g silver nitrate (100 mmol) in 8 mL distilled water. Solution B was prepared by adding 18.0 g polyethyleneimine (molecular weight 60,000; 50% solution in water), and hydrogen fluoride (4.1 g; 50% HF; 100 mmol) under ice cold temperature (0° C.-5° C.) and made up to 25 mL with distilled water. The oral care formulation was prepared by mixing Solution A (25 mL) with Solution B (25 mL) at room temperature (22° C.) in a 100 mL plastic beaker. The product was highly viscous and brown-black in color. This formulation held very well on the substrate and could be very precisely applied at the targeted area of the tooth. The viscosity of the material was 8,350 cPs, which is significantly lower than that of Example 8. The pH of the viscous solution was 5.52. This oral care formulation contained 21.3% silver ions; 18% polyethyleimine and 4.1% fluoride ions. The product was completely soluble in water.

TABLE 2

Compositions of SPF formulated with silver nitrate, polyethyleneimine and HF

| Exp # | Quantity (g) of PEI-HF solution* | Quantity (g) of AgNO$_3$ solution (66.6% in water) | % Ag ions | % F ions | pH |
|---|---|---|---|---|---|
| A1 | 2.0 | 1.0 | 14.2 | 2.2 | 6.1 |
| A2 | 2.0 | 2.0 | 21.3 | 1.7 | 5.9 |
| B1 | 2.0 | 1.0 | 14.2 | 4.5 | 5.2 |
| B2 | 2.0 | 2.0 | 21.3 | 3.4 | 5.0 |
| C1 | 2.0 | 1.0 | 14.2 | 6.7 | 5.0 |
| C2 | 2.0 | 2.0 | 21.3 | 5.0 | 5.2 |
| C3 | 2.0 | 3.0 | 25.5 | 4.0 | 5.3 |
| D1 | 2.0 | 1.0 | 14.2 | 8.9 | 5.2 |
| D2 | 2.0 | 2.0 | 21.3 | 6.8 | 5.1 |
| D3 | 2.0 | 3.0 | 25.5 | 5.4 | 5.2 |

*the PEI-HF stock solution was prepared by adding varying amounts of diluted HF solution to PEI (MW 60,000; 50% solution in water), under ice cold temperature.

Example 10: Fourth Preparation of Silver Polyethyleneimine Fluoride from Silver Nitrate A solution of 66.6 wt. % silver nitrate (Solution A) was prepared by dissolving 10.0 g silver nitrate (59 mmol) in 5 mL distilled water. Solution B was prepared by adding 10.0 g polyethyleneimine (molecular weight 1,800), and hydrogen fluoride (2.4 g; 50% HF; 59 mmol) under ice cold temperature (0° C.-5° C.) and made up to 15 mL. The oral care formulation was prepared by mixing Solution A (15 mL) with Solution B (15 mL) at room temperature (22° C.) in a 100 mL plastic beaker. The product was less viscous (compared to examples of 7-9), and could not be detected by our cone-plate viscometer. The material was grey-black and separation of phases or particles was noted. The material did not adhere well on the substrates and the precise application of the material at the targeted area of the tooth using a thin applicator, e.g., an elastic or multi-strand thread or a plastic flosser, was not convenient. The pH of the solution was 5.03.

Further experimentation with silver nitrate salts, fluoride ion sources such as sodium fluoride, potassium fluoride and polyethyleneimine solutions resulted in stringy, viscous gels. These results may be due to ionic cross-linking of polymer chains with silver ions. Based on our observations, the ionic concentration of hydrofluoric acid in the formulation is important in controlling characteristics such as viscosity, color, and fluoride ion content in the final product.

Example 11: Preparation of Silver PVP Fluoride from Silver Fluoride

A silver polyvinyl pyrrolidinone fluoride conjugate was prepared by gradually dissolving 0.6 g of silver fluoride in 2.5 g of a 20% polyvinyl pyrrolidinone solution containing 0.1 g of HF. The pH of the silver fluoride-polyvinyl pyrrolidinone conjugate was adjusted to pH 7 with the addition of dilute ammonia. The resultant solution had a silver fluoride concentration of about 20%.

Example 12: Preparation of Elastic or Multi-Strand Thread Device Using SDF

A device was formed by dipping a 2 cm section of an elastic or multi-strand, nylon thread, 15 cm long, weighing 0.0150 g, in a solution of SDF (obtained in Experiment 1 above). The solution spread more than desired on the multi-strand, nylon thread due to capillary action. The substrate was dried under a gentle flow of nitrogen for 5 minutes. The amount of dried SDF was found to be 2.6 mg/cm$^2$ exposed area.

Example 13: Preparation of Elastic or Multi-Strand Thread Device Using SPF

A device was formed by dipping a 1 cm section of an elastic or multi-strand, nylon thread, 15 cm long, in the silver polyethyleneimine fluoride formulations obtained in Experiments 2-6 above. A mass of 6.5 mg was coated on a 1 cm length of thread. The viscosity of the SPF formulations allowed us to apply the formulations to the intended 1 cm section without noticeable spreading. The material was then transferred to a carious proximal tooth surface by using the elastic or multi-strand thread as a floss and holding it in place on the carious proximal tooth surface for 10-20 seconds. In this manner, both proximal teeth were treated at the same time.

Example 14: Preparation of Elastic Thread Device Using Silver Fluoride PVP

A device was formed by dipping a 1 cm section of an elastic thread, 15 cm long, weighing 0.150 g, in the silver fluoride-PVP formulation obtained in Example 11 above. The polymeric silver fluoride solution had a good viscosity and could be applied to the intended 1 cm exposed area without any spreading. A mass of 6.5 mg was coated on a 1 cm length of the thread. The substrate was dried under a gentle flow of nitrogen for 2 minutes. The amount of dried silver amine fluoride polymer conjugate was found to be 2.3 mg/cm of exposed area.

Other methods of drying the solution on the elastic or multi-strand thread (or other substrate) are possible, such as air-drying, light-drying and/or heat-drying, as known by one skilled in the art. In addition, other methods of device preparation may be used, such as drying the formulation prior to application on the substrate. For example, liquid may be allowed to partially dry before its application to the substrate e.g., which may form a gooey, gel-like material that can be applied and adhered to the substrate, and/or liquid may be allowed to dry to a powder before its application to the substrate. Further drying of the formulation may form a desiccated powder that may be applied to the substrate.

Although the above discussion discloses various exemplary embodiments of the invention, it should be apparent that those skilled in the art may make various modifications that will achieve some of the advantages of the invention without departing from the true scope of the invention.

What is claimed is:

1. An oral care formulation comprising:
   an aqueous mixture of a water-soluble silver salt, a fluoride reagent, and water-soluble polyethyleneimine, the aqueous mixture having a viscosity ranging from about 1000 cPs to about 35,000 cPs,
   wherein silver is present at about 15% to about 30% on a per weight basis, fluoride is present at about 20.% to about 8.0% on a per weight basis, and polyethyleneimine is present at about 15% to about 30% on a per weight basis.

2. The oral care formulation of claim 1, having a pH of about 5 to about 8.

3. The oral care formulation of claim 1, wherein the fluoride reagent is selected from the group consisting of hydrogen fluoride, silver fluoride, potassium fluoride, sodium fluoride, and combinations thereof.

4. The oral care formulation claim 1, wherein the water-soluble silver salt is selected from the group consisting of silver nitrate, silver fluoride, and silver acetate.

5. The oral care formulation of claim 1, wherein the water-soluble polyethyleneimine has a molecular weight from about 1,800 to about 60,000.

6. The oral care formulation of claim 1, wherein the water-soluble silver salt is silver nitrate, and the fluoride reagent is hydrogen fluoride.

7. A method of using a fluoride and silver containing formulation in dental applications, the method comprising:
   providing a substrate having the fluoride and silver containing formulation in a solid or semi-solid state on a portion of the substrate;
   providing a protective cover that substantially surrounds a portion of the substrate, wherein the protective cover includes a bead or tube substantially surrounding the substrate and movable with respect to the substrate;
   positioning the substrate adjacent to dental areas; and
   allowing the portion of the substrate with the formulation to contact the dental areas.

8. The method of claim 7, wherein allowing the portion of the substrate to contact dental areas includes moving the protective cover so that the substrate with the formulation is able to contact the dental areas.

9. The method of claim 7, further comprising applying the formulation in a liquid state to the substrate and allowing the liquid to dry to the solid or semi-solid state.

10. The method of claim 7, further comprising applying the formulation as a powder, viscous liquid, or gel to the substrate and allowing the powder, viscous liquid, or gel to adhere to the substrate.

11. A disposable applicator for use in dental applications, the applicator comprising:
    a fluoride and silver containing formulation in a solid or semi-solid state;
    a substrate configured to hold the formulation; and
    a protective cover that substantially surrounds a portion of the substrate, the protective cover configured to be movable with respect to the substrate,
    wherein the applicator is configured to be in a first position that allows a portion of the substrate that holds the formulation to be protected by the protective cover and configured to be in a second position that allows the portion of the substrate that holds the formulation to move relative to the protective cover and to be exposed such that the formulation is dispensed when adjacent to dental areas.

12. The disposable applicator of claim 11, wherein the substrate is able to stretch so that the applicator is able to change from the first position to the second position.

* * * * *

UNITED STATES PATENT AND TRADEMARK OFFICE
CERTIFICATE OF CORRECTION

| | | |
|---|---|---|
| PATENT NO. | : 11,931,438 B2 | Page 1 of 1 |
| APPLICATION NO. | : 17/591750 | |
| DATED | : March 19, 2024 | |
| INVENTOR(S) | : Anthony R. Silvestri, Jr. et al. | |

It is certified that error appears in the above-identified patent and that said Letters Patent is hereby corrected as shown below:

In the Claims

In Claim 1, Line 30:
"fluoride is present at about 20.%" should read -- fluoride is present at about 2.0% --

Signed and Sealed this
Twenty-third Day of April, 2024

Katherine Kelly Vidal
*Director of the United States Patent and Trademark Office*